United States Patent
Ueda (10) Patent No.: US 10,322,274 B2
(45) Date of Patent: **\*Jun. 18, 2019**

(54) MEDICAL CONNECTOR

(71) Applicant: TERUMO KABUSHIKI KAISHA, Tokyo (JP)

(72) Inventor: Yasuhiro Ueda, Kofu (JP)

(73) Assignee: TERUMO KABUSHIKI KAISHA, Tokyo (JP)

( \* ) Notice: Subject to any disclaimer, the term of this patent is extended or adjusted under 35 U.S.C. 154(b) by 7 days.

This patent is subject to a terminal disclaimer.

(21) Appl. No.: 15/467,899

(22) Filed: Mar. 23, 2017

(65) Prior Publication Data

US 2017/0189665 A1 Jul. 6, 2017

Related U.S. Application Data

(63) Continuation of application No. PCT/JP2015/004841, filed on Sep. 24, 2015.

(30) Foreign Application Priority Data

Sep. 24, 2014 (JP) .................................. 2014-193878

(51) Int. Cl.
*A61M 39/10* (2006.01)
*A61M 39/20* (2006.01)
(Continued)

(52) U.S. Cl.
CPC ............ *A61M 39/10* (2013.01); *A61M 39/20* (2013.01); *A61M 39/24* (2013.01); *A61M 39/26* (2013.01);
(Continued)

(58) Field of Classification Search
CPC ...... A61M 39/10; A61M 39/20; A61M 39/24; A61M 39/225; A61M 2039/1072; A61M 2039/205
See application file for complete search history.

(56) References Cited

U.S. PATENT DOCUMENTS

| 5,730,418 A | * | 3/1998 | Feith | ..................... A61M 39/26 251/149.1 |
| 6,168,137 B1 | * | 1/2001 | Paradis | ................. A61M 39/26 251/149.1 |

(Continued)

FOREIGN PATENT DOCUMENTS

| JP | 2001-170188 A | 6/2001 |
| JP | 2007-500572 A | 1/2007 |

(Continued)

OTHER PUBLICATIONS

International Search Report issued in International Patent Application No. PCT/JP2015/004841 dated Dec. 15, 2015.
(Continued)

*Primary Examiner* — Jenna Zhang
(74) *Attorney, Agent, or Firm* — Foley & Lardner LLP (57) ABSTRACT

A medical connector includes a cap having a male connector connecting part; a holder having a medical instrument connecting part; and a valve body configured to block the male connector connecting part and configured to be pushed in by a male connector such that a liquid flow channel in the male connector communicates with a liquid flow channel in the medical instrument connecting part when the male connector is connected to the male connector connecting part. The cap and the holder are linked to each other so as to be rotatable about an axis of the male connector connecting part.

7 Claims, 10 Drawing Sheets

(51) Int. Cl.
    *A61M 39/26*     (2006.01)
    *F16L 37/40*     (2006.01)
    *A61M 39/24*     (2006.01)
    *A61M 39/22*     (2006.01)

(52) U.S. Cl.
    CPC ...... *F16L 37/40* (2013.01); *A61M 2039/1072* (2013.01); *A61M 2039/205* (2013.01); *A61M 2039/226* (2013.01)

(56) References Cited

U.S. PATENT DOCUMENTS

| | | | | |
|---|---|---|---|---|
| 6,228,069 B1* | 5/2001 | Barth | | A61M 39/26 604/249 |
| 2004/0124388 A1* | 7/2004 | Kiehne | | A61M 39/26 251/149.1 |
| 2004/0227120 A1* | 11/2004 | Raybuck | | A61M 39/26 251/149.1 |
| 2006/0293629 A1* | 12/2006 | Cote, Sr. | | A61M 39/045 604/246 |
| 2007/0017583 A1* | 1/2007 | Fangrow, Jr. | | A61M 39/10 137/614.06 |
| 2011/0130724 A1* | 6/2011 | Mansour | | A61M 39/26 604/256 |
| 2012/0271246 A1* | 10/2012 | Guala | | A61M 39/26 604/246 |
| 2013/0030386 A1* | 1/2013 | Panian | | A61M 39/22 604/256 |
| 2014/0209197 A1* | 7/2014 | Carrez | | A61M 39/10 137/798 |
| 2014/0246616 A1* | 9/2014 | Fangrow | | A61M 39/26 251/148 |
| 2014/0276458 A1* | 9/2014 | Mansour | | A61M 39/22 604/256 |
| 2014/0303601 A1* | 10/2014 | Fangrow | | A61M 39/10 604/535 |

FOREIGN PATENT DOCUMENTS

| | | | | |
|---|---|---|---|---|
| JP | 2008-540045 A | 11/2008 | | |
| JP | 3166779 U | 3/2011 | | |
| JP | 2013-500453 A | 1/2013 | | |
| WO | WO-00/59561 A1 | 10/2000 | | |
| WO | WO-2006/124981 A | 11/2006 | | |
| WO | WO-2011/016918 A2 | 2/2011 | | |
| WO | WO 2013017518 A1 * | 2/2013 | ........... | A61M 39/10 |
| WO | WO-2013017518 A1 * | 2/2013 | ........... | A61M 39/10 |
| WO | WO-2013/036854 A1 | 3/2013 | | |
| WO | WO 2013036854 A1 * | 3/2013 | ........... | A61M 39/26 |
| WO | WO-2013036854 A1 * | 3/2013 | ........... | A61M 39/26 |
| WO | WO-2015/145998 A1 | 10/2015 | | |

OTHER PUBLICATIONS

European Patent Office, "Communication with Extended Search Report," issued in connection with European Patent Application No. 15844525.4, dated Apr. 9, 2018.

* cited by examiner

MEDICAL CONNECTOR

CROSS-REFERENCE TO RELATED APPLICATIONS

The present application is a bypass continuation of PCT Application No. PCT/JP2015/004841, filed on Sep. 24, 2015, which claims priority to Japanese Application No. 2014-193878, filed on Sep. 24, 2014, the disclosures of which are hereby incorporated by reference in their entireties.

BACKGROUND

The present disclosure relates to a medical connector in which a valve body is pushed in by a male connector and a liquid flow channel in the male connector is made to communicate with a liquid flow channel in a medical instrument connecting part when the male connector is connected to a male connector connecting part, and, more particularly, to a medical connector that is intended to suppress obstruction of liquid flow in tubular bodies and occurrence of removal of the male connector from the male connector connecting part, the obstruction of the liquid flow and the occurrence of the removal being caused by twisting between the tubular bodies connected via the medical connector.

Japanese Unexamined Patent Application Publication No. 2013-500453 describes known medical connectors that are used in, for example, various medical devices, transfusion containers, liquid supplying instruments, or the like, and that are configured for connecting tubular bodies of medical instruments. Such medical connectors are provided with a cap having a male connector connecting part, a holder having a medical instrument connecting part and fixed to the cap, and a valve body for blocking the male connector connecting part. In such medical connectors, the valve body is pushed in by a male connector and a liquid flow channel in the male connector is made to communicate with a liquid flow channel in the medical instrument connecting part when the male connector is connected to the male connector connecting part.

SUMMARY

However, in existing medical connectors such as those described in JP 2013-500453, for example, when the position of a patient is changed with a tubular body that is connected to a transfusion bag and a tubular body inserted in the patient being linked via the medical connector, twisting can occur between the tubular bodies connected via the medical connector, and as a result of the twisting, a liquid flow may be obstructed due constriction of flow channels in the tubular bodies.

In addition, for example, when the male connector connecting part is a Luer-lock-type male connector connecting part or the like, as mentioned above, the occurrence of twisting between the tubular bodies connected via the medical connector weakens the connection of the male connector with respect to the male connector connecting part, as a result of which the male connector may be removed from the male connector connecting part. In particular, when a tubular body inserted in a central vein is to be connected, such as when high-calorie infusion is to be performed, the removal of the male connector may give rise to serious consequences.

Certain embodiments described in the present disclosure have been developed in view of the aforementioned circumstances. One object of the present disclosure is to provide a medical connector that makes it possible to suppress obstruction of liquid flow in tubular bodies and occurrence of removal of a male connector from a male connector connecting part, the obstruction of the liquid flow and the occurrence of the removal being caused by twisting between the tubular bodies connected via the medical connector.

A medical connector according to one embodiment includes a cap having a male connector connecting part, a holder having a medical instrument connecting part, and a valve body for blocking the male connector connecting part, the valve body being pushed in by a male connector and a liquid flow channel in the male connector being made to communicate with a liquid flow channel in the medical instrument connecting part when the male connector is connected to the male connector connecting part. The cap and the holder are linked to each other so as to be rotatable about an axis of the male connector connecting part.

In one aspect, the cap has a cylindrical outer peripheral wall part linked to the holder so as to be rotatable about the axis of the male connector connecting part, the holder has an inner peripheral wall part disposed at an inner peripheral side of the outer peripheral wall part, the medical connector includes a sealing member that prevents a liquid from flowing into a portion between a first peripheral region portion of the inner peripheral wall part and the outer peripheral wall part, and a liquid communication channel that makes a liquid flow channel in the male connector communicate with a liquid flow channel in the medical instrument connecting part when the male connector is connected to the male connector connecting part is formed between a second peripheral region portion of the inner peripheral wall part, excluding the first peripheral region portion, and the outer peripheral wall part.

In one aspect, the valve body has a hollow section and that the holder has a ventilation channel for discharging air from the hollow section when the male connector is connected to the male connector connecting part and for introducing air into the hollow section when the male connector is disconnected from the male connector connecting part.

In one aspect, one end of the ventilation channel opens at an outer peripheral surface of the first peripheral region portion of the inner peripheral wall part, the sealing member is an elastic wall that is adhered to an inner peripheral surface of the outer peripheral wall part along an entire periphery, and the outer peripheral wall part has an opening section that allows the elastic wall to expand toward an outer peripheral side in response to the air discharged from the hollow section via the ventilation channel when the male connector is connected to the male connector connecting part.

In one aspect, the opening section includes a plurality of openings disposed with an interval therebetween along the entire periphery about the axis of the male connector connecting part, and the one end of the ventilation channel has a peripheral-direction width that is larger than the interval between the plurality of openings.

In one aspect, the sealing member has a belt-like elastic body that has an annular shape and that is adhered to the first peripheral region portion of the inner peripheral wall part, and the one end of the ventilation channel communicates with an outside of the medical connector.

Advantageous Effects of Invention

According to the present embodiment, because the cap and the holder are linked to each other so as to be rotatable about the axis of the male connector connecting part, when twisting occurs between tubular bodies connected via the medical connector, it is possible to absorb the twisting by mutually rotating the cap and the holder.

Therefore, according to the present embodiment, it is possible to provide a medical connector that makes it possible to suppress obstruction of liquid flow in tubular bodies and occurrence of removal of the male connector from the male connector connecting part, the obstruction of the liquid flow and the occurrence of the removal being caused by twisting between the tubular bodies connected via the medical connector.

DETAILED DESCRIPTION

A medical connector according to an embodiment of the present invention is hereunder described in detail by way of illustration with reference to FIGS. 1 to 9.

Figure 10:
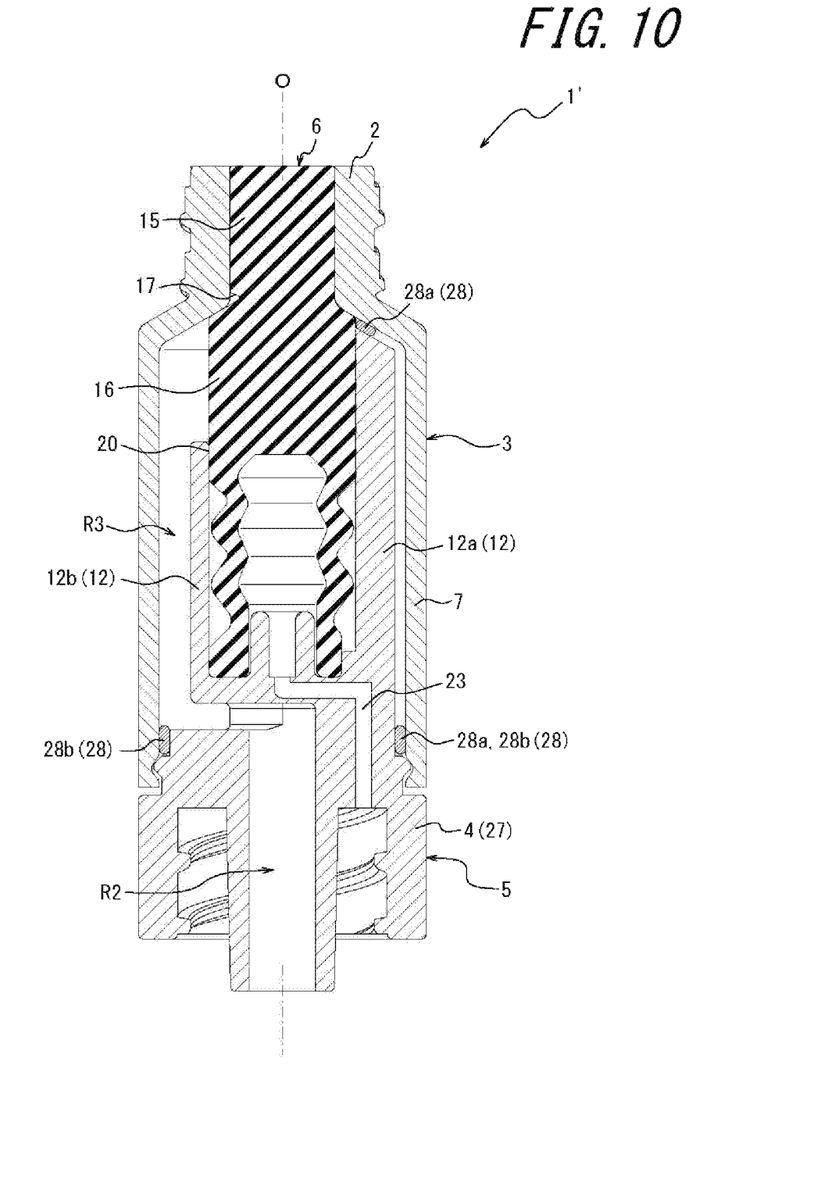
FIG. 10 is a vertical sectional view of a medical connector according to another embodiment of the present invention.
Figure 11:
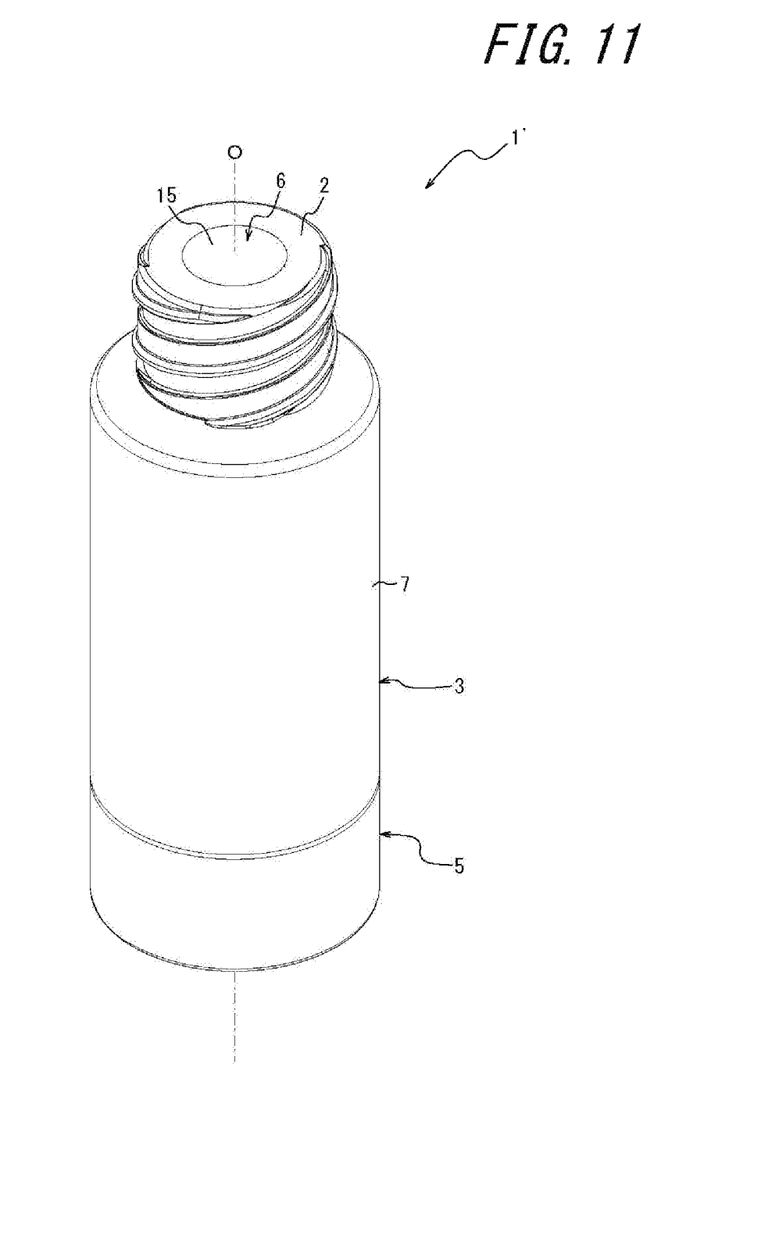
FIG. 11 is a perspective view of the medical connector in FIG. 10.
Figure 12:
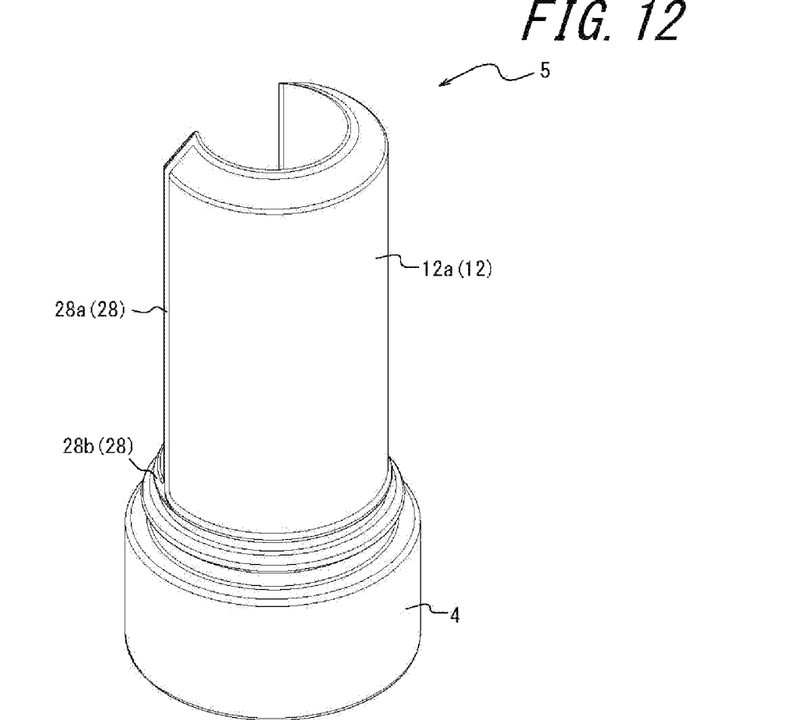
FIG. 12 is a perspective view of a holder of the medical connector in FIG. 10.
Figure 13:
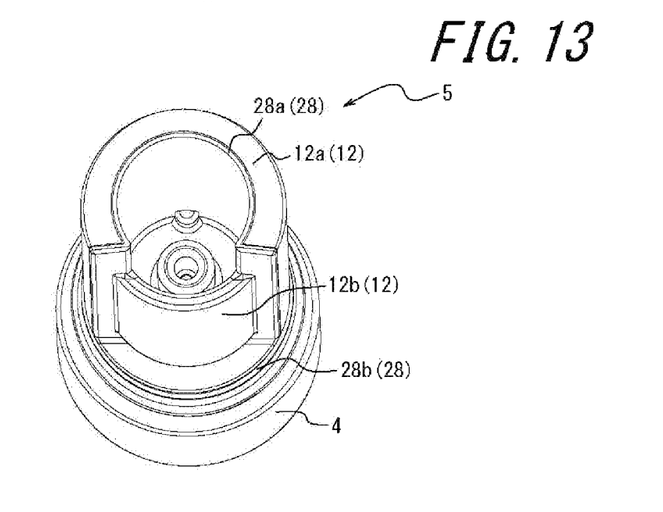
FIG. 13 is a perspective view of the holder in FIG. 10 when seen from another angle.

In the present specification, "upward and downward directions" refer to directions along an axis of a male connector connecting part, "above" means a side at which the male connector connecting part is disposed (that is, "above" in FIGS. 1 and 10), and "below" means a side opposite thereto.

Figure 1:
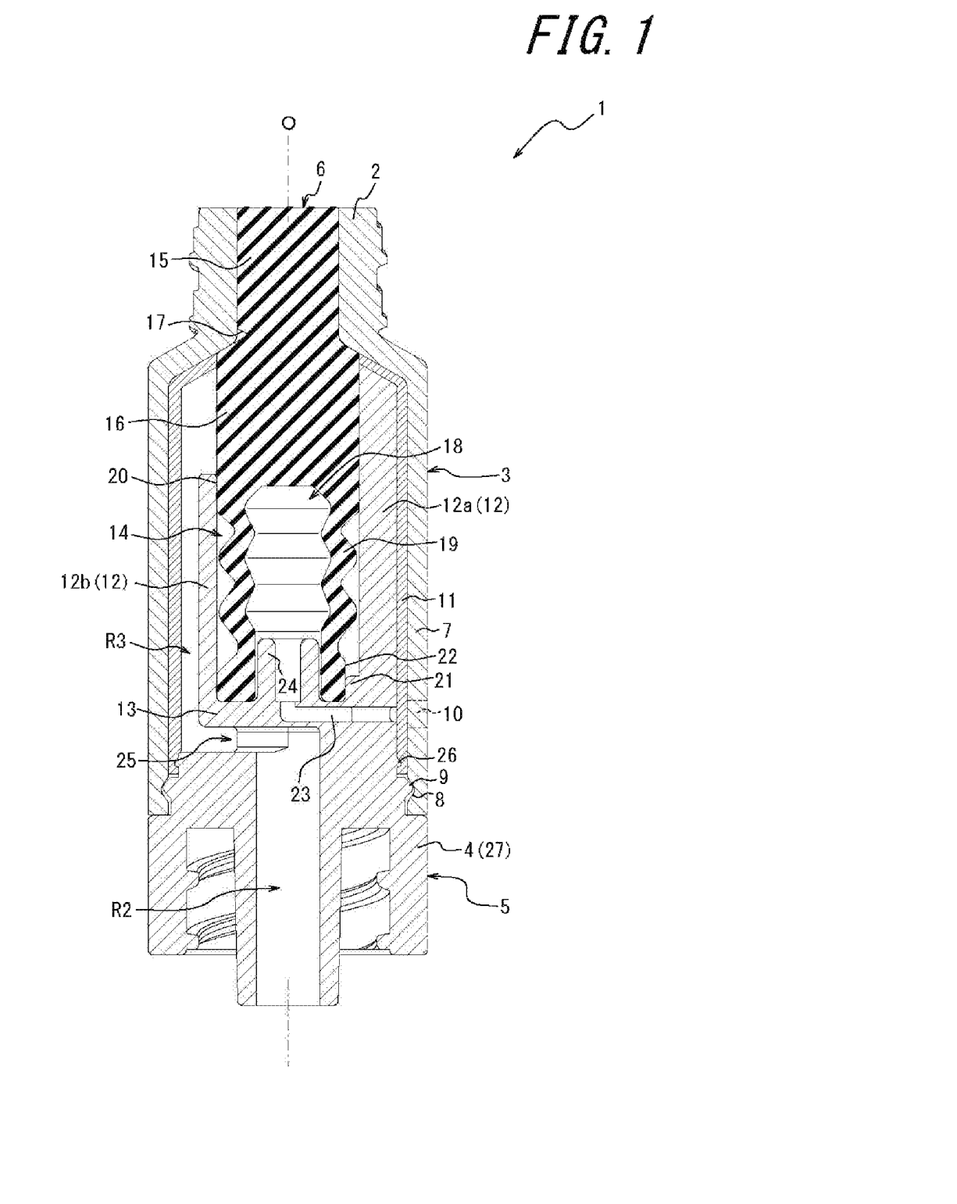
FIG. 1 is a vertical sectional view of a medical connector according to an embodiment of the present invention.
Figure 2:
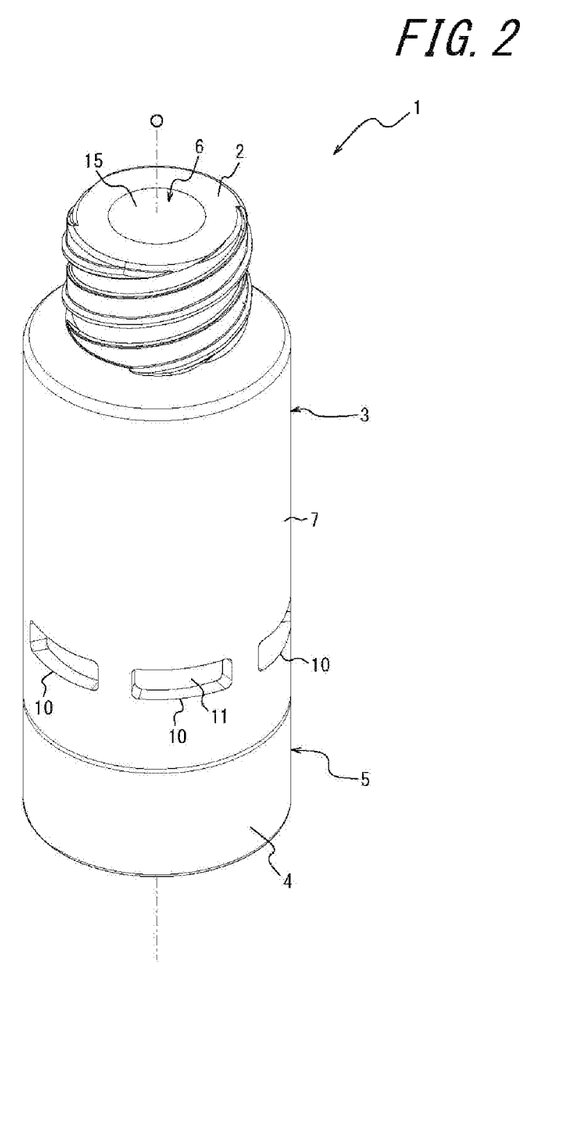
FIG. 2 is a perspective view of the medical connector in FIG. 1.

As shown in FIGS. 1 and 2, the medical connector 1 includes a cap 3 having a male connector connecting part 2, a holder 5 having a medical instrument connecting part 4, and a valve body 6 for blocking the male connector connecting part 2. The cap 3 and the holder 5 may be made of, for example, a synthetic resin material. The valve body 6 may be made of, for example, an elastomer material, such as synthetic rubber.

The cap 3 has a cylindrical outer peripheral wall part 7 linked to the holder 5 so as to be rotatable about an axis O of the male connector connecting part 2. In the present embodiment, an upper end portion of the outer peripheral wall part 7 is formed in the form of a tapered wall whose diameter decreases towards a lower end portion of the cylindrical male connector connecting part 2. In the present embodiment, a male screw for connecting a Luer-lock-type male connector C (see FIG. 8 mentioned below) is formed at an outer peripheral surface of the male connector connecting part 2. As a fixing structure for when the male connector connecting part 2 and the male connector C are connected, instead of using the screw, a structure in which a recessed part and a protruding part are fitted to each other may be used. Instead of fixing the male connector connecting part 2 and the male connector C by using a screw or by fitting a recessed part and a protruding part to each other, a structure in which the fixing is performed by using friction force by only inserting the male connector C into the male connector connecting part 2 (Luer slip type) may be used.

Fitting parts that link the cap 3 to the holder 5 so as to be rotatable about the axis O of the male connector connecting part 2 are formed between an inner peripheral surface of a lower end portion of the outer peripheral wall part 7 and the holder 5. In the present embodiment, the fitting parts include an annular groove 8 that is formed in the inner peripheral surface of the lower end portion of the outer peripheral wall part 7 and an annular protrusion 9 that is provided on the holder 5 and that is fitted to the annular groove 8. A plurality of openings 10, described in detail below and provided as an opening section, are formed in the outer peripheral wall part 7. An elastic wall 11, provided as a sealing member, is adhered to an inner peripheral surface of the outer peripheral wall part 7 along the entire periphery. The elastic wall 11 may be made of, for example, an elastomer material, such as synthetic rubber. It is desirable that the elastic wall 11 be, for example, integrally molded with the cap 3 by insert molding.

Figure 3:
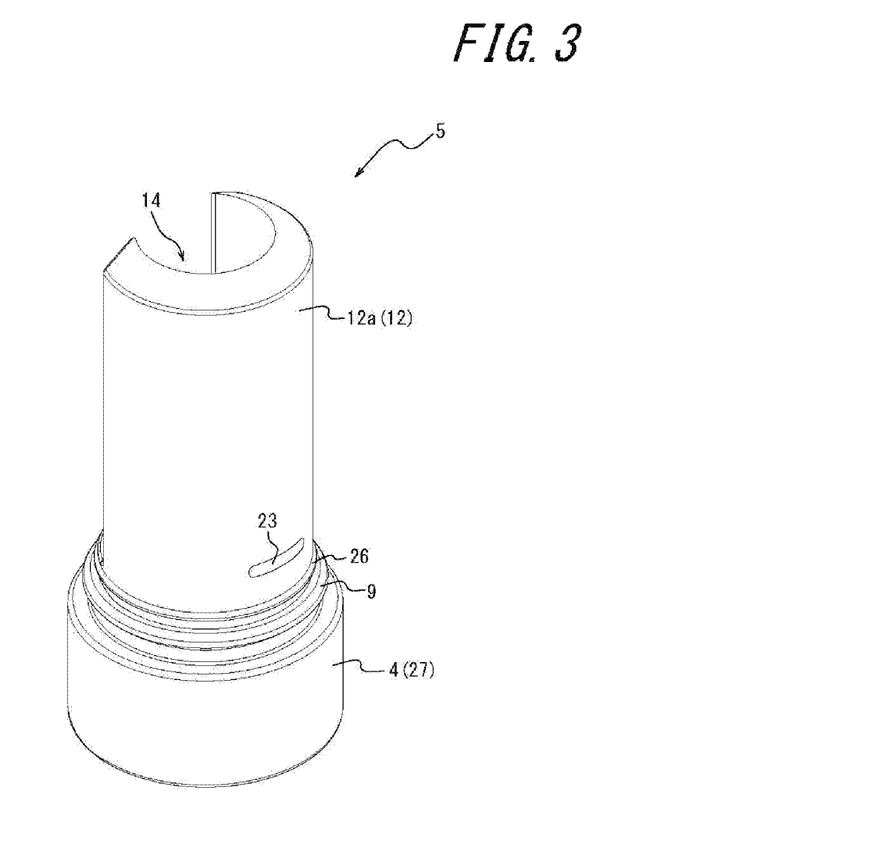
FIG. 3 is a perspective view of a holder of the medical connector in FIG. 1.
Figure 4:
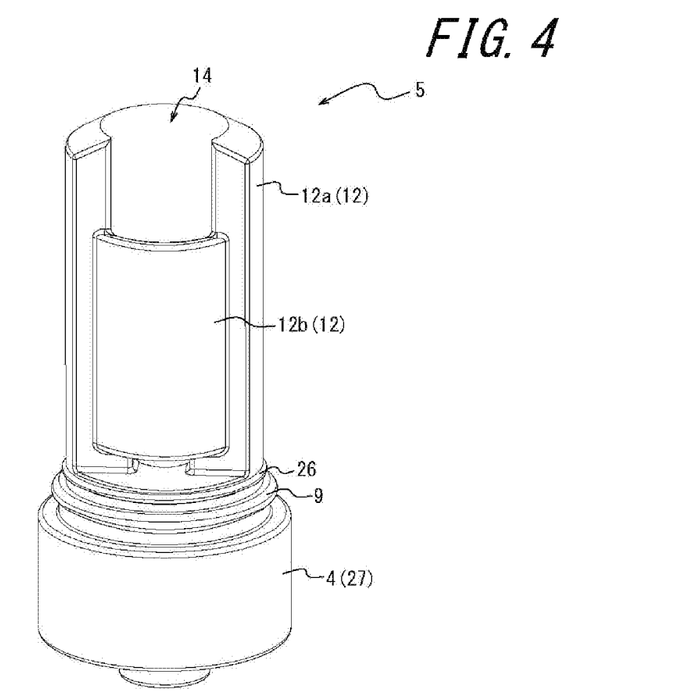
FIG. 4 is a perspective view of the holder in FIG. 3 when seen from another angle.
Figure 5:
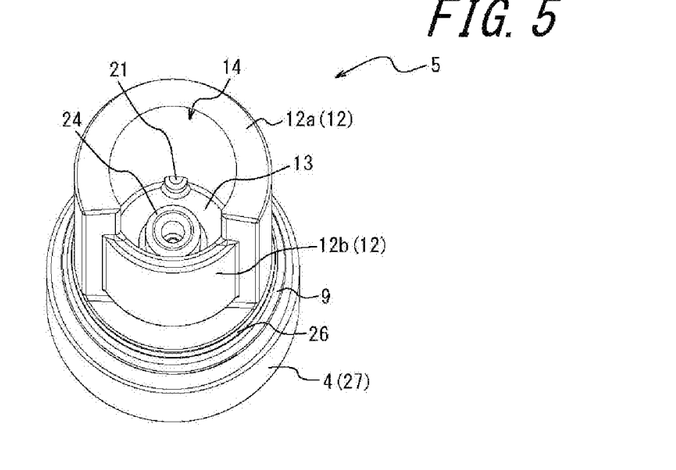
FIG. 5 is a perspective view of the holder in FIG. 3 when seen from still another angle.

The holder 5 has an inner peripheral wall part 12 disposed at an inner peripheral side of the outer peripheral wall part 7. A recessed part bottom wall 13 is formed at a lower portion of the inner peripheral wall part 12, and the inner peripheral wall part 12 and the recessed part bottom wall 13 form a housing recessed part 14 in which the valve body 6 is disposed. As shown in FIGS. 3 to 5, the inner peripheral wall part 12 includes a first peripheral region portion 12a and a second peripheral region portion 12b, which is a portion excluding the first peripheral region portion 12a. As shown in FIG. 1, by interposing the aforementioned elastic wall 11 between the first peripheral region portion 12a of the inner peripheral wall part 12 and the outer peripheral wall part 7 without a gap therebetween, a liquid is prevented from flowing into a portion between the first peripheral region portion 12a and the outer peripheral wall part 7.

A liquid communication channel R3 that makes a liquid flow channel R1 in the male connector C (see FIG. 8 mentioned below) communicate with a liquid flow channel R2 in the medical instrument connecting part 4 when the male connector C is connected to the male connector connecting part 2 is formed between the second peripheral region portion 12b of the inner peripheral wall part 12 and the outer peripheral wall part 7. That is, in the present embodiment, a gap that becomes the liquid communication channel R3 is formed between the aforementioned elastic wall 11 and the aforementioned second peripheral region portion 12b of the inner peripheral wall part 12.

Figure 6:
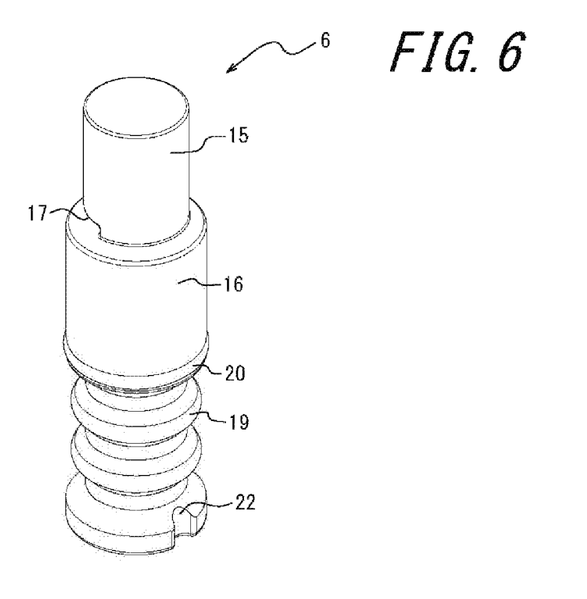
FIG. 6 is a perspective view of a valve body of the medical connector in FIG. 1.
Figure 7:
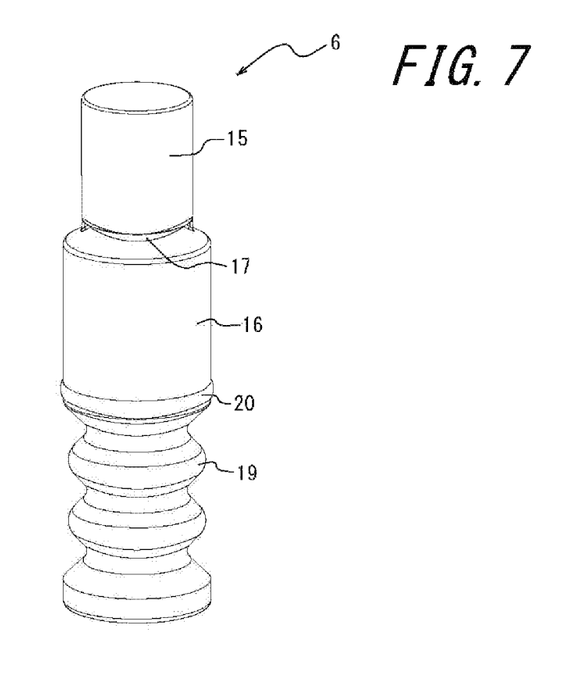
FIG. 7 is a perspective view of the valve body in FIG. 6 when seen from another angle.

As shown in FIGS. 1, 6, and 7, the valve body 6 has a cylindrical head part 15 that blocks the male connector connecting part 2 and a cylindrical body part 16 that is formed continuously with the head part 15. An upper end portion of the body part 16 has a tapered form whose diameter decreases towards a lower end portion of the head part 15. A groove-like cut 17 extending in a peripheral direction is formed in the lower end portion of the head part 15. In the present embodiment, the cut 17 is formed along half of a periphery of the head part 15.

The body part 16 is formed such that its upper side portion has a solid form and its lower side portion has a hollow form. That is, the body part 16 has a hollow section 18 that opens at an end portion at a side opposite to the head part 15. The lower side portion of the body part 16 has a bellows-like peripheral wall 19 that forms the hollow section 18. A seal protrusion 20 that slidably contacts the housing recessed part 14 in a liquid-tight manner is provided around an outer peripheral surface of an upper end portion of the bellows-like peripheral wall 19. An engaging recessed part 22 that prevents rotation of the body part 16 in a peripheral direction thereof by engaging with an engaging protrusion 21 formed on the housing recessed part 14 is formed at an outer peripheral surface of a lower end portion of the bellows-like peripheral wall 19. As means for preventing the rotation of the body part 16 in the peripheral direction, instead of using the engaging protrusion 21 and the engaging recessed part 22, for example, adhesion, welding, or the like may be used.

As shown in FIG. 1, a ventilation channel 23 that causes the hollow section 18 of the valve body 6 and an outer peripheral surface of the first peripheral region portion 12a of the inner peripheral wall part 12 to communicate is formed in the recessed part bottom wall 13 of the holder 5. That is, one end of the ventilation channel 23 opens at the outer peripheral surface of the first peripheral region portion 12a of the inner peripheral wall part 12, and the other end of the ventilation channel 23 opens at a location, corresponding to the hollow section 18 of the valve body 6, at an upper surface of the recessed part bottom wall 13. A support protrusion 24 having a cylindrical shape in which the axis O is the center is erected on the recessed part bottom wall 13.

A cavity part 25 that makes the liquid communication channel R3 formed between the second peripheral region portion 12b of the inner peripheral wall part 12 and the outer peripheral wall part 7 communicate with the liquid flow channel R2 in the medical instrument connecting part 4 is formed underneath the recessed part bottom wall 13.

Below the liquid communication channel R3, an annular protrusion 26 that press-contacts an inner peripheral surface of the elastic wall 11 is provided around the holder 5. Sealability between the liquid communication channel R3 and the outside of the medical connector 1 is increased by the annular protrusion 26.

The medical instrument connecting part 4 is continuous with the lower portion of the recessed part bottom wall 13. In the present embodiment, the medical instrument connecting part 4 is formed as a Luer-lock-type male connector 27 disposed concentrically with the axis O of the male connector connecting part 2. In the present embodiment, the medical connector 1 is formed as a mixed injection plug having one male connector 27 as the medical instrument connecting part 4. However, instead, the medical connector 1 may be formed as, for example, a T-type mixed injection port having an additional connecting part, or as a three-way cock.

Figure 8:
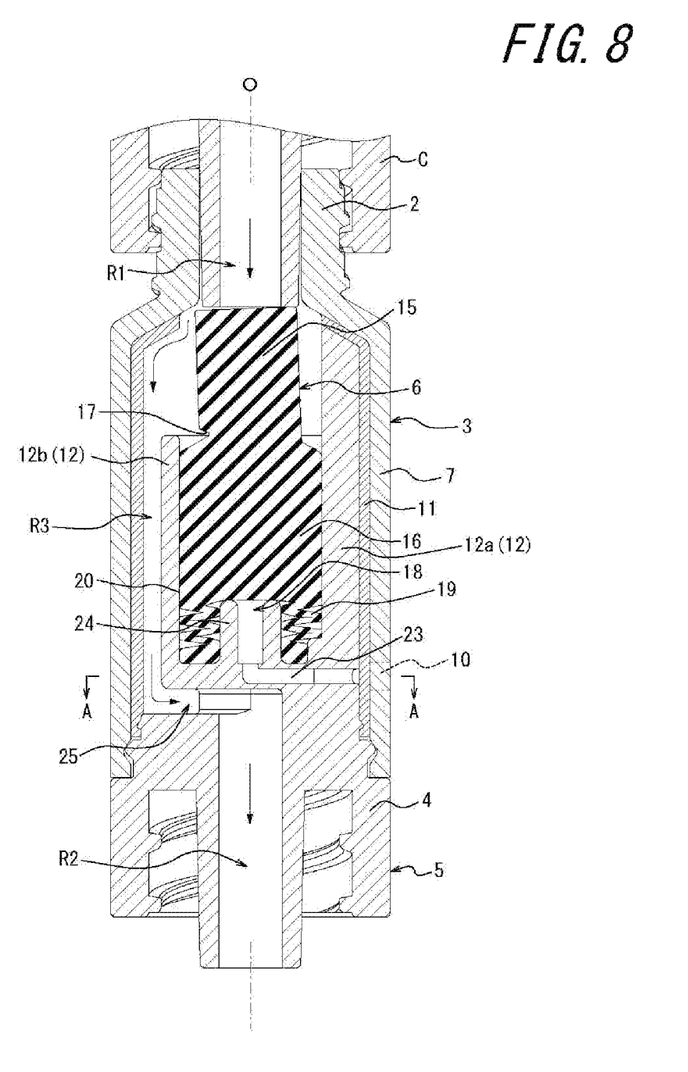
FIG. 8 is a vertical sectional view of the medical connector in FIG. 1 and illustrates a state in which a male connector is connected.
Figure 9:
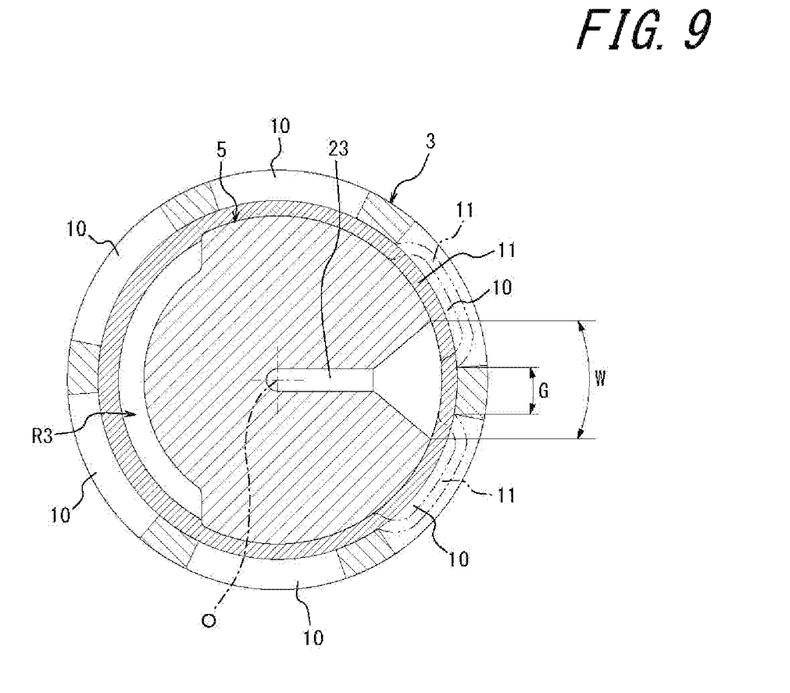
FIG. 9 is a sectional view taken along line A-A of FIG. 8.

As shown in FIGS. 8 and 9, the plurality of openings 10 are formed in the cap 3. The plurality of openings 10 are provided as an opening section that allows the elastic wall 11 to expand towards an outer peripheral side in response to air discharged from the hollow section 18 of the valve body 6 via the ventilation channel 23 when the male connector C is connected to the male connector connecting part 2. The plurality of openings 10 are disposed with intervals G therebetween along the entire periphery about the axis O of the male connector connecting part 2. In the present embodiment, the ventilation channel 23 has a shape in which one end side portion widens towards an end. The one end of the ventilation channel 23 has a peripheral-direction width W that is larger than the intervals G between the plurality of openings 10.

According to the medical connector 1 of the present embodiment having such a structure, as shown in FIG. 8, when, with a connector (not shown) of a tubular body of a medical instrument being connected to the medical instrument connecting part 4, the male connector C of a tubular body of another medical instrument is connected to the male connector connecting part 2, the male connector C pushes in the head part 15 of the valve body 6 while compressing the bellows-like peripheral wall 19 of the body part 16. Here, since air from the hollow section 18 of the body part 16 can be discharged via the ventilation channel 23, it is possible to reduce a force required to connect the male connector C to the male connector connecting part 2 and easily perform the connection. In addition, as shown in FIG. 9, the air discharged from the hollow section 18 at this time is held between the elastic wall 11 and the holder 5 while expanding the elastic wall 11. Because the peripheral-direction width W of the one end of the ventilation channel 23 is larger than the intervals G between the plurality of openings 10, it is possible to expand the elastic wall 11 in response to the air discharged from the hollow section 18 regardless of the position of the cap 3 and the position of the holder 5 in a peripheral direction relative to each other.

When the bellows-like peripheral wall 19 is folded, the support protrusion 24 provided on a bottom surface of the housing recessed part 14 contacts a head-part-15-side end surface of the hollow section 18 of the valve body 6 and suppresses further deformation of the bellows-like peripheral wall 19. From this state, when the head part 15 of the valve body 6 is further pushed in, the head part 15 of the valve body 6 is deformed so as to be tilted towards the liquid communication channel R3 with the cut 17 as a starting point. As a result, it is possible to make the fluid flow channel R1 in the male connector C communicate with the fluid flow channel R2 in the medical instrument connecting part 4 via the fluid communication channel R3 formed between the second peripheral region portion 12b of the inner peripheral wall part 12 of the holder 5 and the outer peripheral wall part 7 of the cap 3. At this time, since the elastic wall 11 is interposed between the first peripheral region portion 12a of the inner peripheral wall part 12 and the outer peripheral wall part 7 without a gap therebetween, it is possible to prevent a liquid from flowing into a portion between the first peripheral region portion 12a and the outer peripheral wall part 7 and to suppress retention of the liquid.

Further, at this time, the body part 16 of the valve body 6 is covered with the housing recessed part 14. Therefore, as shown by the arrows in FIG. 8, because contact of a fluid flowing in the medical connector 1 with the body part 16 of the valve body 6 is suppressed, occurrence of contamination due to adhesion of the fluid to the body part 16 of the valve body 6 is suppressed. Further, in the present embodiment, because the seal protrusion 20 provided around an outer peripheral surface of the body part 16 of the valve body 6 slidably contacts an inner peripheral surface of the housing recessed part 14 in a liquid-tight manner, it is possible to further suppress entry of the fluid flowing in the medical connector 1 up to an outer peripheral surface of the bellows-like peripheral wall 19 of the valve body 6.

When, in this state, twisting occurs between tubular bodies connected via the medical connector 1, since the cap 3 and the holder 5 are linked to each other so as to be rotatable about the axis O of the male connector connecting part 2, it is possible to absorb the twisting by mutually rotating the cap 3 and the holder 5.

When the male connector C is connected to the male connector connecting part 2, as shown in FIG. 9, the air discharged from the hollow section 18 of the valve body 6 is held between the elastic wall 11 and the holder 5 while expanding the elastic wall 11. If, from this state, the cap 3 and the holder 5 mutually rotate with the occurrence of twisting between the tubular bodies mentioned above, when a bulge of the elastic wall 11 and the fluid communication channel R3 overlap, the air held by the bulge of the elastic wall 11 enters the fluid communication channel R3. However, it is desirable that the amount of air that intrudes into the fluid communication channel R3 in this way be as small as possible. Therefore, it is desirable to set the size of the hollow section 18 of the valve body 6 by considering not only connection resistance of the male connector C to the male connector connecting part 2 but also the aforementioned amount of intrusion of air.

When, before use, the cap 3 and the holder 5 are mutually rotated once with the male connector C connected, air is caused to escape to the fluid communication channel R3, and the male connector C is removed, the hollow section 18 of the valve body 6 can have a negative pressure accordingly. Therefore, thereafter, even if the male connector C is connected to the male connector connecting part 2, because the elastic wall 11 is prevented from expanding, it is possible to prevent occurrence of intrusion of air into the fluid communication channel R3 when the cap 3 and the holder 5 mutually rotate. In this way, when the air is made to escape to the fluid communication channel R3 before use, if the male connector C is not connected, the elastic wall 11 is slightly recessed to a side of the ventilation channel 23.

In this way, according to the medical connector 1, because the twisting between the tubular bodies connected via the medical connector 1 can be absorbed due to the mutual rotation of the cap 3 and the holder 5, it is possible to suppress obstruction of liquid flow in the tubular bodies and occurrence of removal of the male connector C from the male connector connecting part 2, the obstruction of the liquid flow and the occurrence of the removal being caused by the twisting between the tubular bodies connected via the medical connector 1.

Further, when the male connector C is disconnected from the male connector connecting part 2, because the bellows-like peripheral wall 19 of the body part 16 of the valve body 6 is expanded and restored, an increase in the volume of the fluid flow channels in the medical connector 1, the occurrence of which has hitherto been of concern when the male connector C is removed, is suppressed or prevented by the expansion of the bellows-like peripheral wall 19 of the body part 16 of the valve body 6 accordingly. As a result, occurrence of drawing-in of a fluid at the medical instrument connecting part 4 when the male connector C is removed is suppressed or prevented.

Next, with reference to FIGS. 10 to 13, a medical connector 1' according to another embodiment of the present invention will be described.

The medical connector 1' according to the present embodiment has the same structure as that of the embodiment previously described by using FIGS. 1 to 9 except for the structure of a sealing member (the elastic wall 11 in the previously described embodiment), the structure of a ventilation channel 23, and the structure of an outer peripheral wall part 7.

As shown in FIGS. 10 to 13, in the present embodiment, an elastic member 28, provided as the sealing member, has a first belt-like elastic body 28a that has an annular shape and that is adhered to a first peripheral region portion 12a of an inner peripheral wall part 12. In addition, the elastic member 28 has a second belt-like elastic body 28b that has an annular shape and that is adhered to a holder 5 at a location below a liquid communication channel R3. In the present embodiment, the first belt-like elastic body 28a and the second belt-like elastic body 28b are integrated with each other. It is desirable that the elastic member 28 be, for example, integrally molded with the holder 5 by insert molding.

In the present embodiment, one end of the ventilation channel 23 communicates with the outside of the medical connector 1'. A plurality of openings 10 (opening section) provided in the previously described embodiment are not provided in the outer peripheral wall part 7.

Therefore, according to the medical connector 1' according to the present embodiment, when, with a connector (not shown) of a tubular body of a medical instrument being connected to a medical instrument connecting part 4, a male connector C (see FIG. 8 mentioned above) of a tubular body of another medical instrument is connected to a male connector connecting part 2, air is discharged to the outside of the medical connector 1' via the ventilation channel 23 (see FIG. 10) from a hollow section 18 of the valve body 6. When, in this state, twisting occurs between the tubular bodies connected via the medical connector 1, it is possible to absorb the twisting by mutually rotating the cap 3 and the holder 5. The other effects are the same as those of the previously described embodiment.

The embodiments of the present invention described above are exemplary, and may be variously changed while remaining within the scope of the claims. For example, although the holder 5 is described as a single member, the holder 5 may be formed by assembling two or more parts. Other components may also be similarly formed by assembling two or more parts.

Although, in the above-described embodiments, the valve body 6 is described as being provided with the cut 17, the valve body 6 need not necessarily be limited to such a structure. The valve body 6 may have any structure as long as the valve body 6 can be pushed in by the male connector C and the liquid flow channel R1 in the male connector C can be made to communicate with the liquid flow channel R2 in the medical instrument connecting part 4 when the male connector C is connected to the male connector connecting part 2. That is, when the cut 17 is not provided, for example, an upper surface of the head part 15 of the valve body 6 may have an inclined form, or the upper surface of the head part 15 may have a groove that opens at an outer peripheral surface of the head part 15. When the cut 17 is provided in the valve body 6, the position where the cut 17 is provided is not particularly limited as long as it is possible to tilt the head part 15 and make the liquid flow channel R1 in the male connector C communicate with the liquid flow channel R2 in the medical instrument connecting part 4 when the male connector C is connected. That is, the cut 17 need not necessarily be provided in the lower end portion of the head part 15 as it is as mentioned above and may be provided at any position above the seal protrusion 20. That is, the cut 17 may be provided in, for example, the outer peripheral surface of the body part 16.

REFERENCE NUMERAL LIST

1, 1' medical connector
2 male connector connecting part 3 cap
4 medical instrument connecting part
5 holder
6 valve body
7 outer peripheral wall part
8 annular groove
9 annular protrusion
10 opening (opening section)
11 elastic wall
12 inner peripheral wall part
12a first peripheral region portion
12b second peripheral region portion
13 recessed part bottom wall
14 housing recessed part
15 head part
16 body part
17 cut
18 hollow section
19 bellows-like peripheral wall
20 seal protrusion
21 engaging protrusion
22 engaging recessed part
23 ventilation channel
24 support protrusion
25 cavity part
26 annular protrusion
27 male connector (medical instrument connecting part)
28 elastic member
28a first belt-like elastic body
28b second belt-like elastic body
O axis
C male connector
R1 liquid flow channel in male connector
R2 liquid flow channel in medical instrument connecting part
R3 liquid communication channel
G interval
W peripheral-direction width

The invention claimed is:

1. A medical connector comprising:
a cap comprising:
   a male connector connecting part, and
   a cylindrical outer peripheral wall part;
a holder comprising:
   a medical instrument connecting part, and
   an inner peripheral wall part disposed inside the cylindrical outer peripheral wall part of the cap;
a valve body configured to block the male connector connecting part and configured to be pushed in by a male connector such that a liquid flow channel in the male connector communicates with a liquid flow channel in the medical instrument connecting part when the male connector is connected to the male connector connecting part; and
a sealing member that is located between (i) a first portion of an outer peripheral surface of the inner peripheral wall part and (ii) the cylindrical outer peripheral wall part of the cap, and that extends from a top of the inner peripheral wall part to a bottom of the inner peripheral wall part, such that the sealing member prevents a liquid from flowing between (i) the first portion of the outer peripheral surface of the inner peripheral wall part and (ii) the cylindrical outer peripheral wall part of the cap,
wherein a liquid communication channel is formed between (i) a second portion of the outer peripheral surface of the inner peripheral wall part and (ii) the cylindrical outer peripheral wall part of the cap, the liquid communication channel being configured to allow the liquid flow channel in the male connector to communicate with the liquid flow channel in the medical instrument connecting part when the male connector is connected to the male connector connecting part,
wherein the cylindrical outer peripheral wall part of the cap is linked to the holder so as to be rotatable about an axis of the male connector connecting part,
wherein the sealing member is an elastic wall that is adhered to an inner peripheral surface of the cylindrical outer peripheral wall part of the cap.

2. The medical connector according to claim 1, wherein:
the valve body has a hollow section,
the holder comprises a ventilation channel for discharging air from the hollow section when the male connector is connected to the male connector connecting part and for introducing air into the hollow section when the male connector is disconnected from the male connector connecting part,
wherein a first end of the ventilation channel opens at the first portion of the outer peripheral surface of the inner peripheral wall part,
wherein the cylindrical outer peripheral wall part of the cap has an opening section that allows the elastic wall to expand outward in response to air being discharged from the hollow section via the ventilation channel when the male connector is connected to the male connector connecting part.

3. The medical connector according to claim 2, wherein:
the opening section includes a plurality of openings disposed at intervals along an entire periphery of the opening section about the axis of the male connector connecting part, and
the first end of the ventilation channel has a peripheral-direction width that is larger than the interval between the plurality of openings.

4. The medical connector according to claim 1, wherein:
the valve body has a hollow section,
the holder comprises a ventilation channel for discharging air from the hollow section when the male connector is connected to the male connector connecting part and for introducing air into the hollow section when the male connector is disconnected from the male connector connecting part.

5. A medical connector comprising:
a cap comprising:
   a male connector connecting part, and
   a cylindrical outer peripheral wall part;
a holder comprising:
   a medical instrument connecting part, and
   an inner peripheral wall part disposed inside the cylindrical outer peripheral wall part of the cap;
a valve body configured to block the male connector connecting part and configured to be pushed in by a male connector such that a liquid flow channel in the male connector communicates with a liquid flow channel in the medical instrument connecting part when the male connector is connected to the male connector connecting part; and
a sealing member that is located between (i) a first portion of an outer peripheral surface of the inner peripheral wall part and (ii) the cylindrical outer peripheral wall part of the cap, and that extends from a top of the inner peripheral wall part to a bottom of the inner peripheral wall part, such that the sealing member prevents a liquid from flowing between (i) the first portion of the outer peripheral surface of the inner peripheral wall part and (ii) the cylindrical outer peripheral wall part of the cap, wherein a liquid communication channel is formed between (i) a second portion of the outer peripheral surface of the inner peripheral wall part and (ii) the cylindrical outer peripheral wall part of the cap, the liquid communication channel being configured to allow the liquid flow channel in the male connector to communicate with the liquid flow channel in the medical instrument connecting part when the male connector is connected to the male connector connecting part, wherein the cylindrical outer peripheral wall part of the cap is linked to the holder so as to be rotatable about an axis of the male connector connecting part, wherein the sealing member comprises a belt-like elastic body that has an annular shape and that is adhered to the first portion of the outer peripheral surface of the inner peripheral wall part.

6. The medical connector according to claim 4, wherein:
the valve body has a hollow section,
the holder comprises a ventilation channel for discharging air from the hollow section when the male connector is connected to the male connector connecting part and for introducing air into the hollow section when the male connector is disconnected from the male connector connecting part,
a first end of the ventilation channel communicates with an outside of the medical connector.

7. The medical connector according to claim 1, wherein:
the valve body has a hollow section,
the holder comprises a ventilation channel for discharging air from the hollow section when the male connector is connected to the male connector connecting part and for introducing air into the hollow section when the male connector is disconnected from the male connector connecting part.

* * * * *